(12) United States Patent
Bellamy et al.

(10) Patent No.: US 6,644,137 B1
(45) Date of Patent: Nov. 11, 2003

(54) SAMPLE PROBE (75) Inventors: Michael Bellamy, Maryville, MO (US); Robert Pastor, Guaynabo, PR (US); Norman Mortensen, Salina, KS (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 09/594,549

(22) Filed: Jun. 14, 2000

Related U.S. Application Data (60) Provisional application No. 60/139,268, filed on Jun. 15, 1999.

(51) Int. Cl.[7] ................................................ G01N 1/00
(52) U.S. Cl. .................................................. 73/864.63
(58) Field of Search ........................ 73/863.31, 863.33, 73/864.44, 864.45, 864.63, 864.65–864.67, 86, 864.64; 175/20, 58

(56) References Cited

U.S. PATENT DOCUMENTS

| | | | | |
|---|---|---|---|---|
| 243,948 A | * | 7/1881 | Newell | ................... 73/864.63 |
| 3,683,892 A | * | 8/1972 | Harris | ..................... 73/864.44 |
| 3,968,696 A | * | 7/1976 | Rosenblum | .............. 73/864.63 |
| 4,072,059 A | * | 2/1978 | Hamilton | ................. 73/864.31 |
| 4,346,612 A | * | 8/1982 | Rand | ...................... 73/864.63 |
| 4,866,997 A | * | 9/1989 | Kaufman | ................. 73/864.63 |
| 5,322,133 A | * | 6/1994 | Hart | ........................ 73/864.44 |
| 5,606,139 A | * | 2/1997 | Wittig et al. | ............. 73/864.44 |
| 5,996,426 A | * | 12/1999 | Robinson et al. | ........ 73/864.63 |

* cited by examiner

*Primary Examiner*—Robert Raevis
(74) *Attorney, Agent, or Firm*—Patent Law Offices of Heath W. Hoglund (57) ABSTRACT

A sampling probe includes a housing, a cover and a guide. The housing defines a trough having an opening, at least a portion of the opening being in an insertion direction of the probe. The cover is axially movable with respect to the housing between an open position in which a substance is allowed to pass into the trough and a closed position in which the cover covers the opening to retain a predetermined volume of the substance in the trough. The cover is flexible. The guide is configured to guide axial movement of the cover between the open and closed positions. The guide is configured to direct the cover in a curved path.

13 Claims, 7 Drawing Sheets

SAMPLE PROBE

CLAIM OF PRIORITY

This is a continuation of Application No. 60/139,268, filed Jun. 15, 1999. Applicants claim all benefits of priority from that application.

BACKGROUND OF THE INVENTION

1. Field of the Invention

The present invention relates to sampling probes. More particularly, the present invention relates to sampling probes used to collect samples of a powder blend in pharmaceutical applications. While the invention is subject to a wide range of applications, it is especially suited for use in an apparatus or in a process; and it will be particularly described in that connection.

2. Description of Related Art

Figure 1:
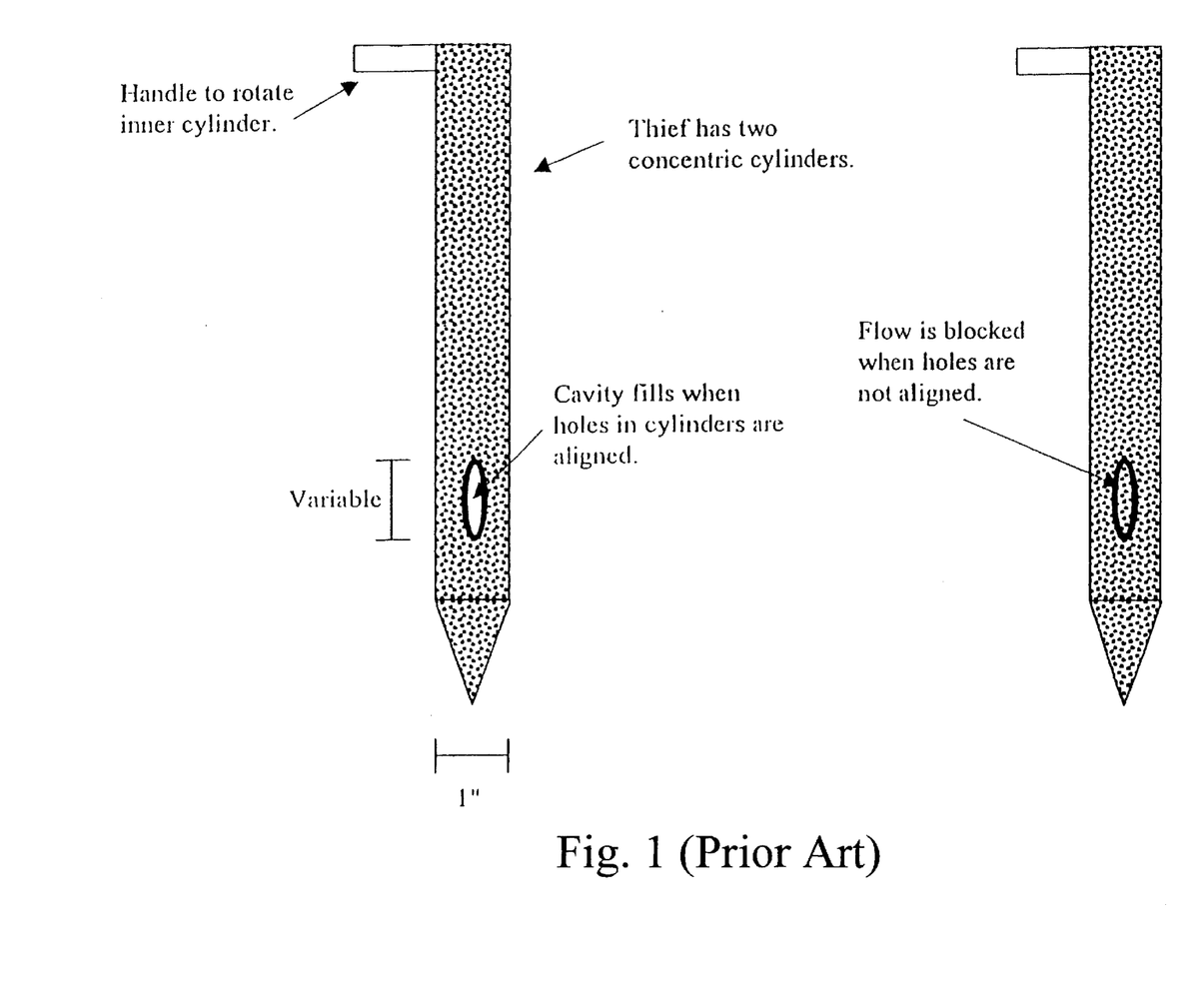
FIG. 1 is a schematic diagram of a prior art sampling probe consisting of two concentric tubes to collect powder samples.

It is a requirement for pharmaceutical companies to collect samples of a powder blend and demonstrate that the blend is homogeneous. A device known as a sampling probe or "thief" is used to collect such powder samples from a large blender. All of the samples must contain appropriate amounts of particular drugs in order for the blend to be classified as homogenous. A process has been proposed in which a sampling probe shown in FIG. 1 is introduced into a powder blend. This sampling probe has concentric inner and outer tubes, wherein the inner tube has an opening covered by the outer tube. The outer tube is rotated to uncover the opening in the inner tube. The powder blend then flows into the inner tube and the outer tube is then rotated once again to cover the opening, thereby trapping the powder to collect a sample.

However, when the powder blend segregates easily, the captured sample is sometimes not representative of the blend. That is, certain particles in the blend separate as the sample flows into the probe and is collected. The sample could then contain either too much or too little of a particular component of a drug. Thus, a homogeneous blend may possibly be characterized erroneously as being non-homogeneous. Failure of a blend to meet FDA homogeneity requirements can represent considerable financial hardship to a pharmaceutical company.

Figure 2:
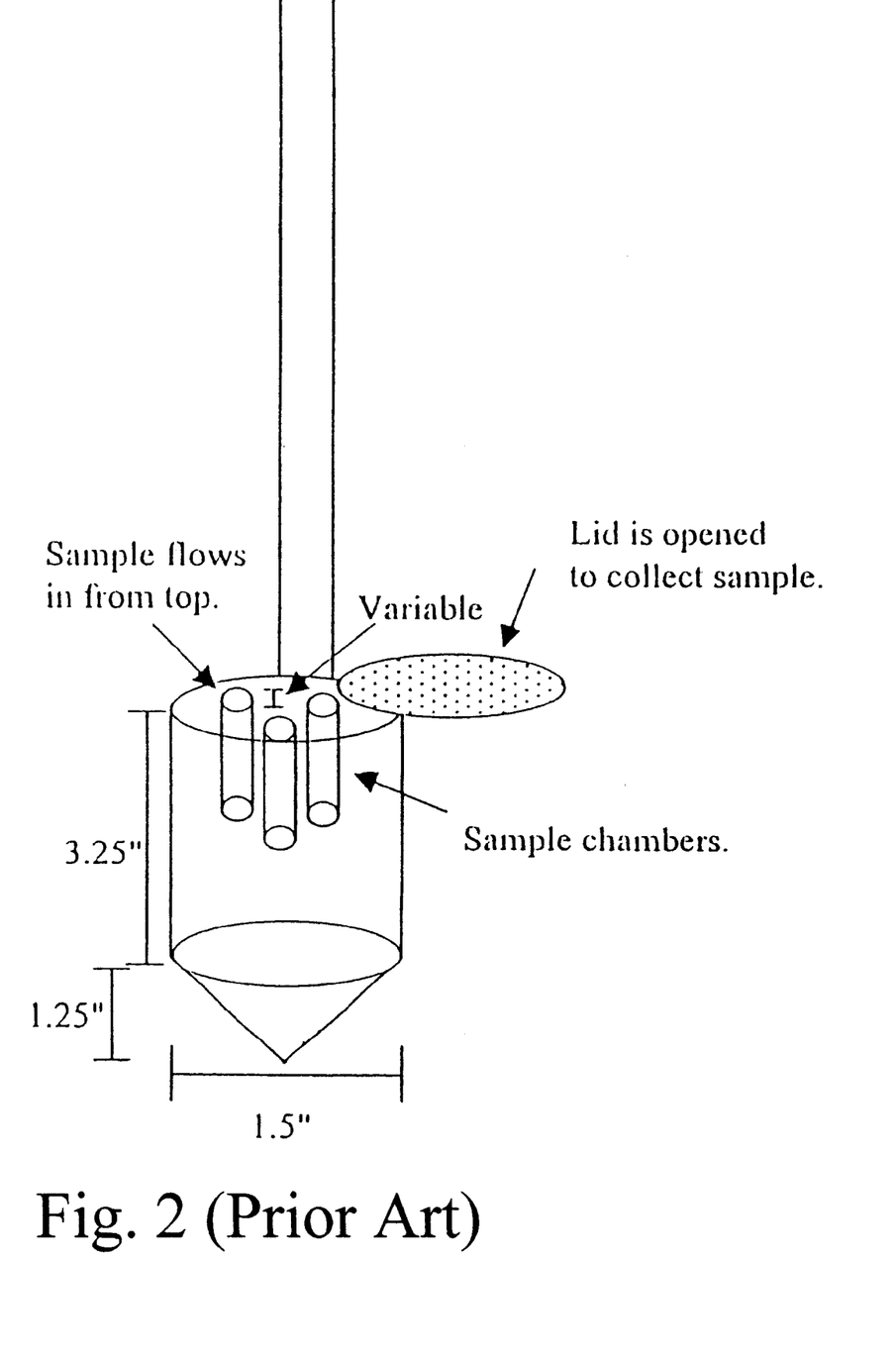
FIG. 2 is a schematic diagram of a second prior art sampling probe consisting of several top-filled tubes to collect powder samples.
Figure 3:
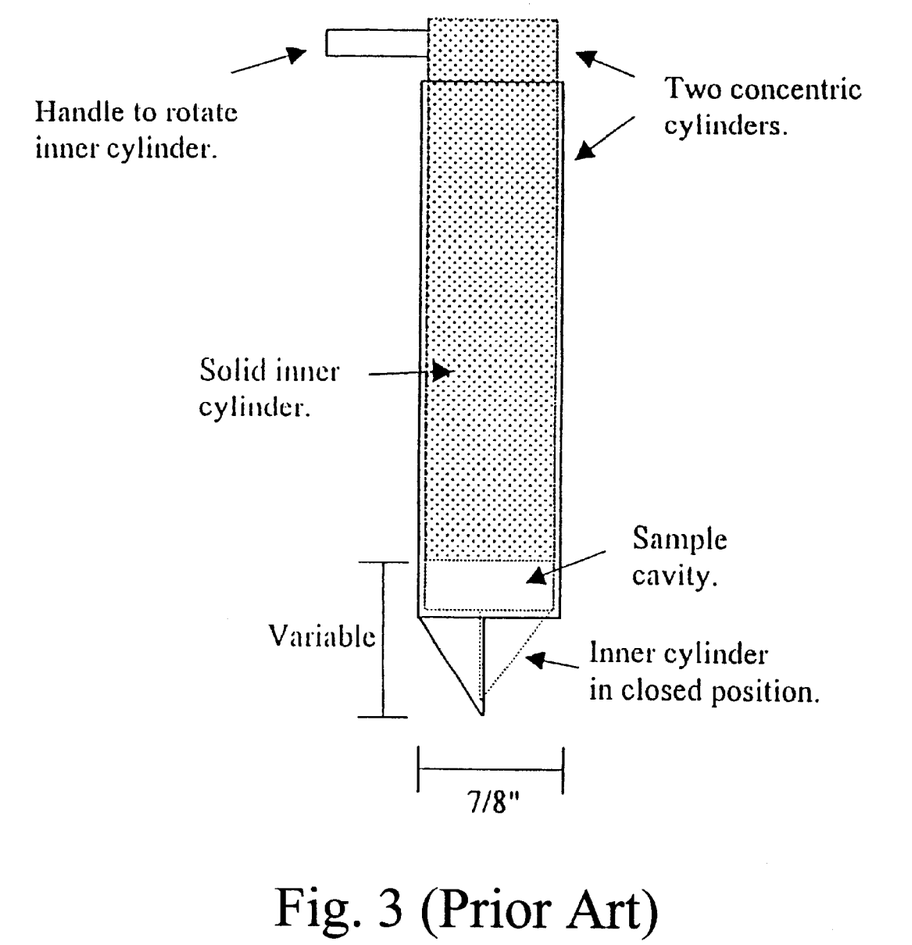
FIG. 3 is a schematic diagram of a third prior art sampling probe consisting of two concentric tubes with a variable sample cavity to collect powder samples.

FIGS. 2 and 3 show other embodiments of sampling probes proposed for use in the pharmaceutical industry. These sampling probes have drawbacks similar to those associated with the sampling probe shown in FIG. 1. In particular, these probes could also allow for powder segregation, thereby providing a false indication of homogeneity/non-homogeneity. Thus, there is a need for an improved sampling probe capable of collecting samples from powder blends that segregate easily.

SUMMARY OF THE INVENTION

Accordingly, the present invention is directed to an improved sampling probe capable of collecting samples from powder blends that segregate easily. The invention further provides a means of collecting samples by "grabbing," entrapping or enclosing a predetermined volume of powder blend from anywhere in the powder blender without having the blend flow into the probe.

Additional features and advantages of the invention will be set forth it the description which follows, and in part will be apparent from the description, or may be learned by practice of the invention. The objectives and other advantages of the invention will be realized and attained by means of the elements and combinations particularly pointed out in the written description and claims herein as well as the appended drawings.

To achieve these and other advantages and in accordance with the purpose of the invention, as embodied and broadly described herein, the invention includes a sampling probe having a housing defining a trough with an opening. At least a portion of the opening is in the direction of the probe's insertion. The probe also has a corner axially movable with respect to the housing between an open position in which a substance is allowed to pass into the trough and a closed position in which the cover covers the opening to retain a predetermined volume of the substance in the trough. A guide is configured to guide axial movement of the cover between the open and closed positions.

In another aspect, the sampling probe's cover is flexible and the guide is configured to direct the cover in a curved path.

In yet another aspect, the sampling probe's housing has a first and second inner wall surfaces spaced from one another. The surfaces define at least a portion of the trough between them. The guide is formed by a first groove on the first inner wall surface and a second groove on the second inner wall surface.

In another aspect, the invention includes first and second removable plates. The first plate rests on the first inner wall surface and the second plate rests on the second inner wall surface.

In yet another aspect, the sampling probe includes a housing with a first inner wall surface having a first edge and a second edge and a base parallel to the first inner wall surface and having a first edge and a second edge. The first edge of the base is coupled to the first edge of the first inner wall surface. The housing also has a second inner wall surface parallel to the first inner wall surface and having a first edge and a second edge. The first edge of the second inner wall surface is coupled to the second edge of the base. The first inner wall surface, second inner wall surface, and base define a trough with an opening. The probe also has a flexible cover movable with respect to the housing between an open position permitting entry of substances into the trough via the opening, and a closed position closing the opening to retain a predetermined volume of the substance in the trough. A guide is configured to guide movement of the cover between the open position and the closed position.

In another aspect, the guide in the sampling probe is a set of grooves. A first groove is on the first inner wall surface and a second groove is on the second inner wall surface. The grooves face each other and are in engagement with the cover.

In yet another aspect, the cover is attached to a spring biasing the cover towards one of the open or closed positions. The cover may also be coupled to a handle.

In another aspect, the probe's housing includes a cavity configured to store at least a portion of the cover when the cover is in the open position. The housing may also have a bracket including first and second sides and a base.

Another aspect of the invention is a method of obtaining a sample of a substance such as a powderous material. The method includes providing any embodiment of the sampling probe summarized above, inserting the sampling probe into the substance while the cover is in the open position so that a portion of the substance enters the trough, and moving the cover to the closed position to retain a predetermined amount of the substance in the trough.

In another aspect, the method includes biasing the cover toward one of the open and closed positions.

BRIEF DESCRIPTION OF THE DRAWINGS

The accompanying drawings, which are incorporated in and constitute a part of this specification, illustrate embodiments of the invention and, together with a description, serve to explain the objects, advantages, and principles of the invention. In the drawings.

DESCRIPTION OF THE PREFERRED EMBODIMENTS

Reference will now be made to the present preferred embodiments of the invention, which are illustrated in the accompanying drawings. Wherever possible, the same reference numbers will be used throughout the drawings to refer to the same or like parts.

Figure 4:
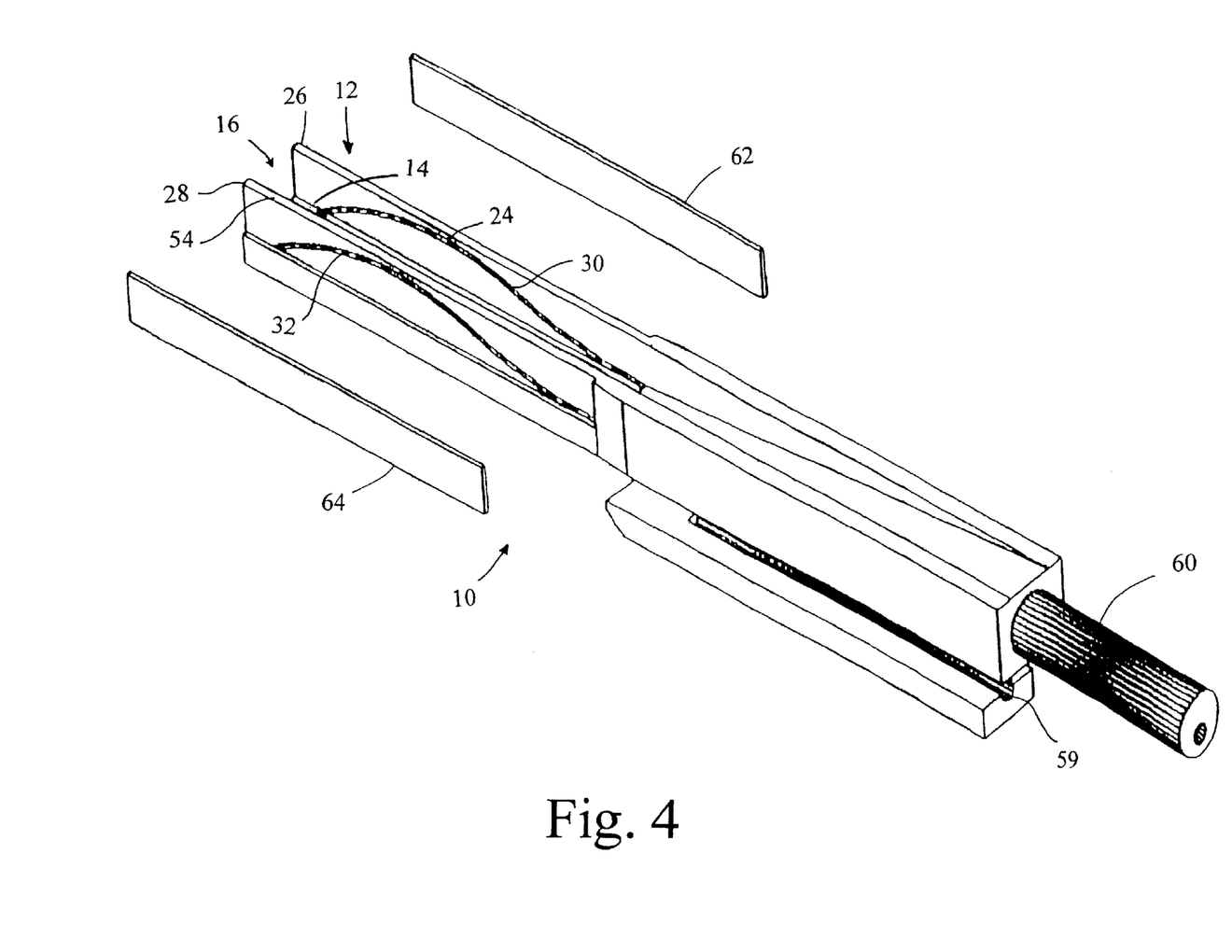
FIG. 4 is an isometric view of a first embodiment of the sampling probe wherein outer walls are shown apart from sampling walls.

A preferred embodiment of the sampling probe is shown in FIG. 4, and identified generally by reference numeral 10. The sampling probe 10 includes a housing 12 defining a trough 14 with an opening 16. At least a portion of opening 16 is in the direction of the probe's insertion. The probe also has a cover 18, shown in FIG. 5, axially movable with respect to housing 12 between an open position 20 in which a substance, not shown, is allowed to pass into trough 14 and a closed position 22 in which the cover covers opening 16 to retain a predetermined volume of the substance in trough 14. A guide 24 is configured to guide axial movement of the cover between open position 20 and closed position 22.

Figure 5:
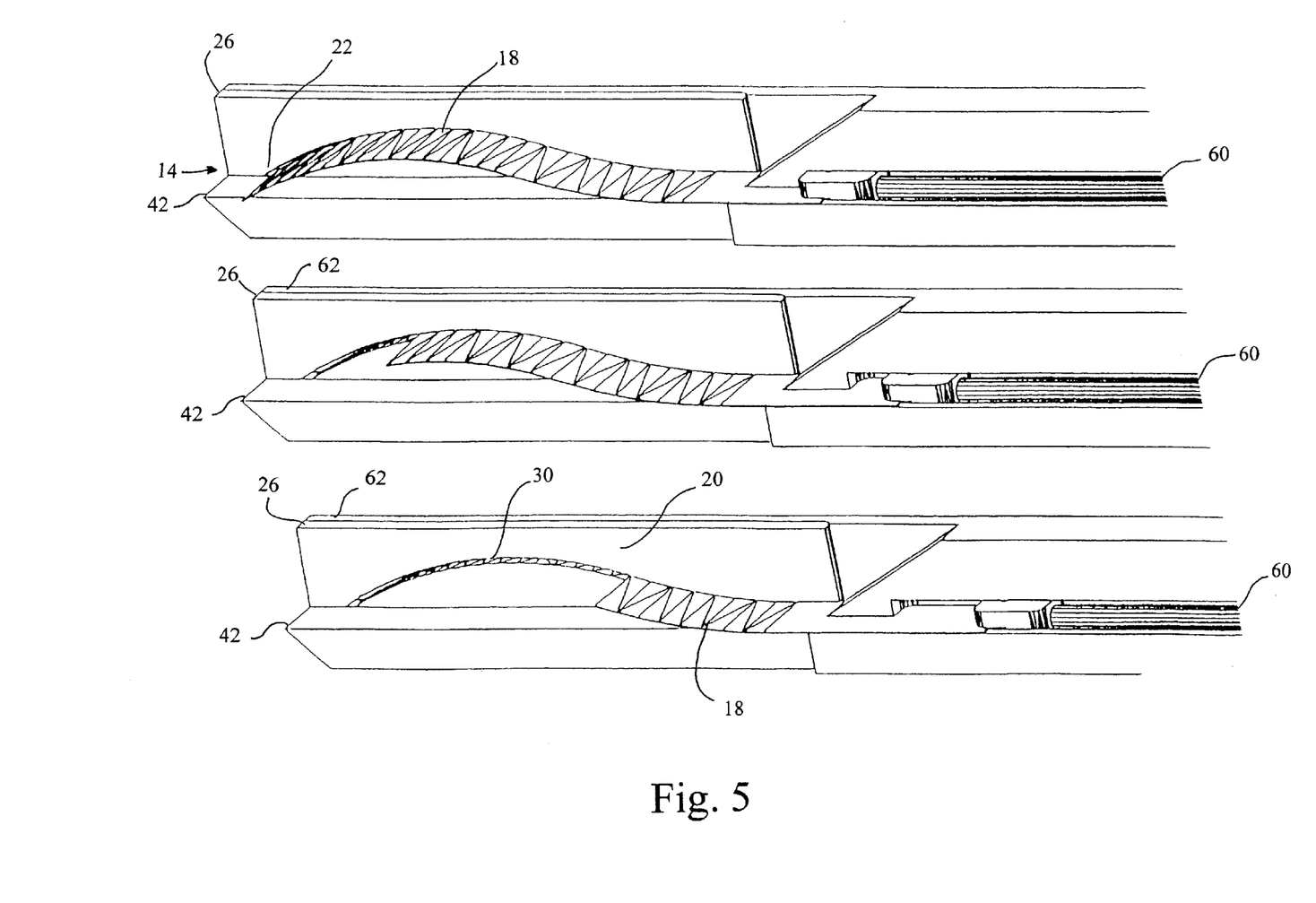
FIG. 5 is cutaway side view of the progression from step A to step C by which the flexible sheet of material is moved from its predetermined opened position to its predetermined closed position.
Figure 6:
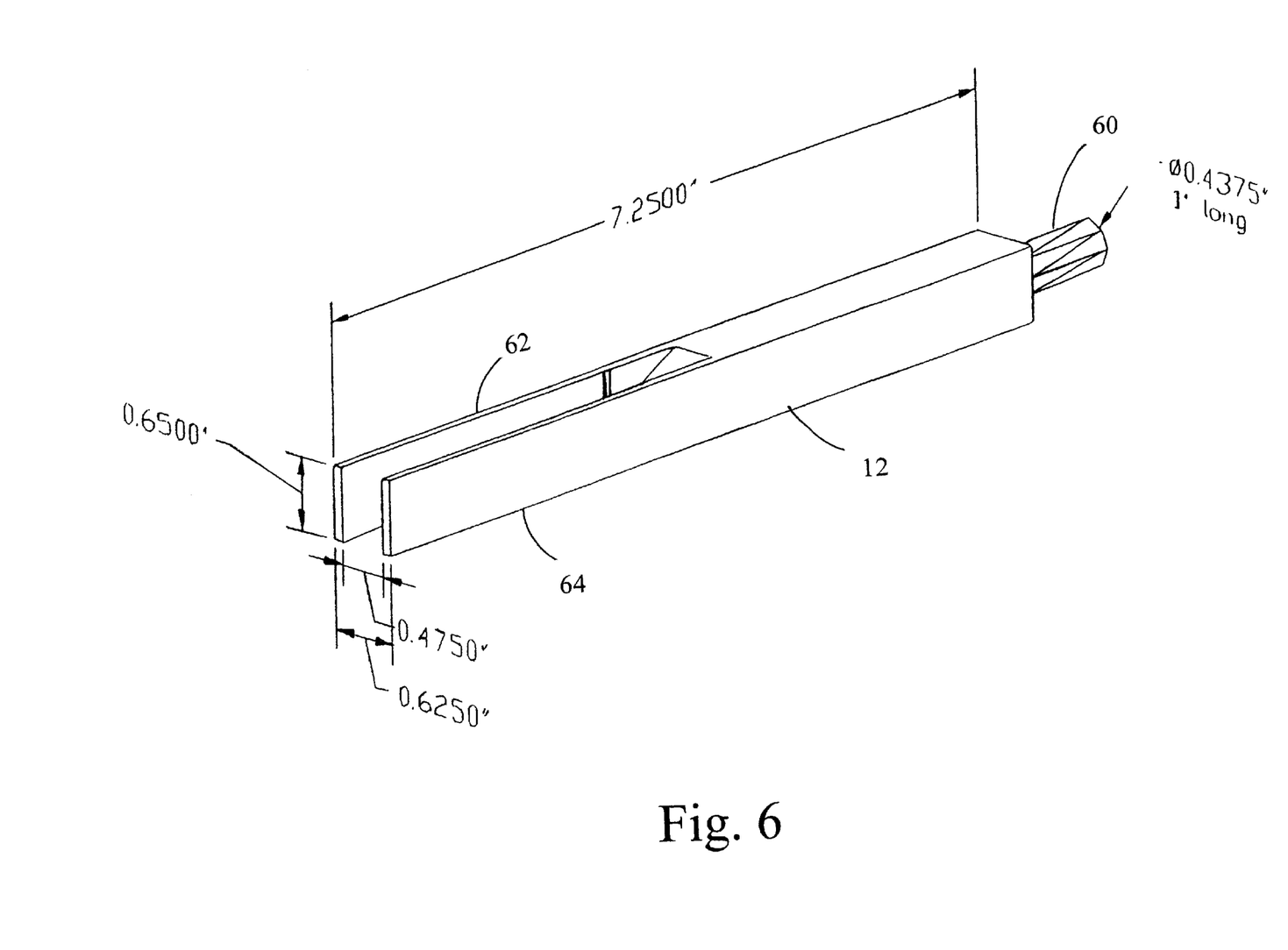
FIG. 6 is an isometric view of an integrated housing and bracket assembly.

As shown in FIG. 5, cover 18 is flexible and guide 24 is configured to direct the cover in a curved path. While the cover and all other components of the sampling probe may be made of any suitable material, it is preferred that the components be made of a Food and Drug Administration ("FDA") approved material such as stainless steel or teflon.

In a preferred embodiment, housing 12 has a first inner wall surface 26 and a second inner wall surface 28 spaced from one another. The surfaces define at least a portion of trough 14 between them. Guide 24 is formed by a first groove 30 on first inner wall surface 26 and a second groove 32 on second inner wall surface 28.

Figure 7:
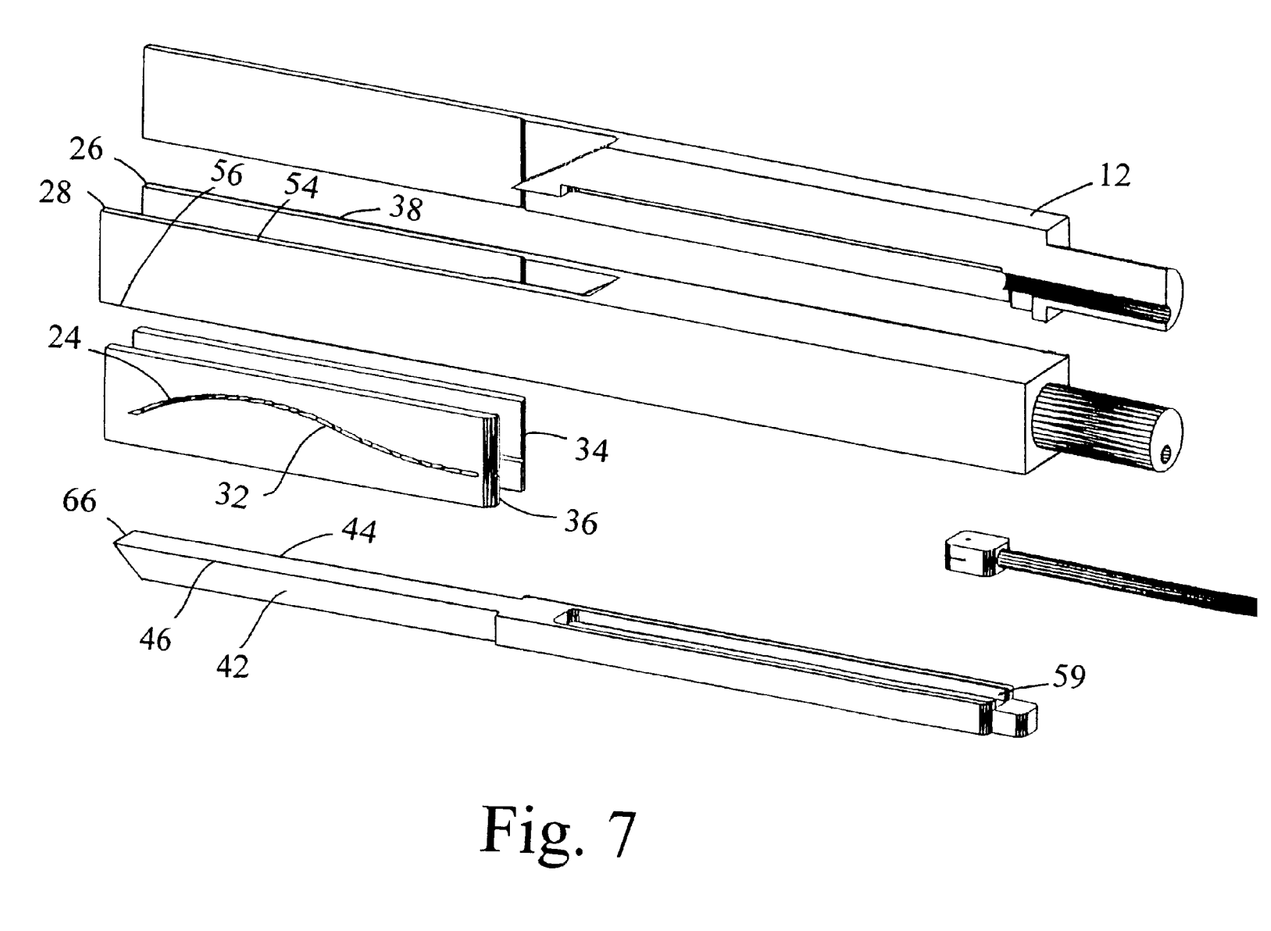
FIG. 7 is an isometric view of the components of the sampling probe and a cross-sectional view of the body 5.

In another embodiment of the invention, shown in FIG. 7, housing 12 includes first and second removable plates 34 and 36, respectively. First plate 34 rests on first inner wall surface 26 and the second plate 36 rests on second inner wall surface 28.

Housing 12 includes first inner wall surface 26 having a first edge 38 and a second edge, not shown in FIG. 7, and a base 42 perpendicular to first inner wall surface 26 and having a first edge 44 and a second edge 46. First edge 44 of base 42 is coupled to first edge 38 of first inner wall surface 26. Housing 12 also has second inner wall surface 28 parallel to first inner wall surface 26 and having a first edge 54 and a second edge 56. First edge 54 of second inner wall surface 28 is coupled to second edge 46 of base 42. First inner wall surface 26, second inner wall surface 28, and base 42 define trough 14 with an opening 16. In this embodiment, cover 18 is moveable with respect to housing 12 between open position 20 permitting entry of substances through 14 via opening 16, and a closed position 22 closing opening 16 to retain a predetermined volume of the substance in trough 14. Guide 24 is configured to guide movement of cover 18 between open position 20 and closed position 22. Guide 24 may be configured as a set of grooves 30 and 32 respectively. A first groove 30 is on first inner wall surface 26 and a second groove 32 is on second inner wall surface 28. Grooves 30 and 32 face each other and are in engagement with cover 18.

As shown in FIG. 7, housing 12 includes a cavity 59 configured to store at least a portion of cover 18 when the cover is in open position 20. Housing 12 may also have a bracket 60, including a first side 62, a second side 64 and a base 66.

Another aspect of the invention is a method of obtaining a sample of a substance such as a powderous material. The method includes providing any embodiment of sampling probe 10, inserting the sampling probe into the substance while cover 18 is in the open position 20 so that a portion of the substance enters the trough 14, and moving the cover to the closed position 22 to retain a predetermined amount of the substance in trough 14.

In another embodiment, the method includes biasing cover 18 toward one of the open and closed positions 10 and 22 respectively.

With the above detailed description of the sampling probe apparatus and method of the present invention, those skilled in the art.would appreciate that modifications may be made to the invention without departing from its spirit. Therefore, it is not intended that the scope of the invention be limited to the specific embodiments illustrated and described above. Rather, it is intended that the scope of this invention be determined by the appended claims and their equivalents.

What is claimed is:

1. A sampling probe comprising:
   a housing defining a trough having an opening, at least a portion of the opening being in an insertion direction of the probe;
   a cover axially movable with respect to the housing between an open position in which a substance is allowed to pass into the trough and a closed position in which the cover covers the opening to retain a predetermined volume of the substance in the trough, wherein the cover is flexible; and
   a guide configured to guide axial movement of the cover between the open and closed positions, wherein the guide is configured to direct the cover in a curved path.

2. The sampling probe of claim 1 wherein the housing comprises first and second inner wall surfaces spaced from one another and defining at least a portion of the trough therebetween, and wherein the guide comprises a first groove on the first inner wall surface and a second groove on the second inner wall surface.

3. The sampling probe of claim 2, wherein the housing includes first and second removable plates, the first inner wall surface being on the first plate and the second inner wall surface being on the second plate.

4. A sampling probe comprising:
   a housing including a first inner wall surface having a first edge and a second edge, a base parallel to the first inner wall surface and having a first edge and a second edge, the first edge of the base coupled to the first edge of the first inner wall surface, and a second inner wall surface parallel to the first inner wall surface and having a first edge and a second edge, the first edge of the second inner wall surface coupled to the second edge of the base, the first inner wall surface, second inner wall surface, and base defining a trough having an opening;
   a flexible cover movable with respect to the housing between an open position permitting entry of substances into the trough via the opening, and a closed position closing the opening to retain a predetermined volume of the substance in the trough; and
   a guide configured to guide movement of the cover between the open position and the closed position.

5. The sampling probe of claim 4 wherein the guide comprises a first groove on the first inner wall surface and a second groove on the second inner wall surface, the first and second grooves facing one another and being in engagement with the cover.

6. The sampling probe of claim 4, wherein the housing includes a cavity configured to store at least a portion of the cover when the cover is in the open position.

7. A method of obtaining sample of a substance comprising:
   providing the sampling probe of claim 1;
   inserting the sampling probe into the substance while the cover is in the open position so that a portion of the substance enters the trough; and
   moving the cover to the closed position to retain a predetermined amount of the substance in the trough.

8. The method of claim 7, wherein the substance is a blend of powderous material.

9. A sampling thief comprising:
   a housing having a base and a pair of side walls connected along opposite sides of the base, wherein the side walls each define a curved groove path; and
   a flexible cover positioned between the side walls and in the curved groove path.

10. The sampling thief of claim 9, wherein the curved groove path defined by the side walls determines a sample volume.

11. The sampling thief of claim 9, wherein the side walls are removeably connected along opposite sides of the base.

12. The sampling thief of claim 9, wherein the flexible cover moves between an open position substantially removed from the curved groove path and a closed position substantially completing the curved groove path.

13. A sampling thief comprising:
   a means for defining a trough for insertion into a powdered compound;
   a means for defining a curved path within the trough; and
   a means for closing at least a portion of the means for defining the trough along the means for defining the curved path.

* * * * *